United States Patent
Oldham et al.

(10) Patent No.: US 7,382,258 B2
(45) Date of Patent: *Jun. 3, 2008

(54) SAMPLE CARRIER DEVICE INCORPORATING RADIO FREQUENCY IDENTIFICATION, AND METHOD

(75) Inventors: Mark F. Oldham, Los Gatos, CA (US); Richard D. Morris, San Francisco, CA (US); Jerome A. Mack, San Mateo, CA (US)

(73) Assignee: Applera Corporation, Foster City, CA (US)

( * ) Notice: Subject to any disclaimer, the term of this patent is extended or adjusted under 35 U.S.C. 154(b) by 322 days.

This patent is subject to a terminal disclaimer.

(21) Appl. No.: 11/086,069

(22) Filed: Mar. 22, 2005

(65) Prior Publication Data

US 2005/0242963 A1  Nov. 3, 2005

Related U.S. Application Data

(63) Continuation-in-part of application No. 10/805,093, filed on Mar. 19, 2004.

(51) Int. Cl.
    *G08B 13/14* (2006.01)
(52) U.S. Cl. .............................. 340/572.1; 340/572.8; 435/7.1
(58) Field of Classification Search .............. 340/572.1, 340/572.7, 572.8, 10.1; 435/7.1; 436/149, 436/47, 155
    See application file for complete search history.

(56) References Cited

U.S. PATENT DOCUMENTS

| | | | |
|---|---|---|---|
| 5,641,634 A | 6/1997 | Mandecki | |
| 5,700,429 A | 12/1997 | Bühler et al. | |
| 5,741,462 A | 4/1998 | Nova et al. | |
| 5,751,629 A | 5/1998 | Nova et al. | |
| 5,764,892 A * | 6/1998 | Cain et al. ................ | 340/572.1 |
| 5,770,455 A | 6/1998 | Cargill et al. | |
| 5,859,587 A * | 1/1999 | Alicot et al. ............. | 340/572.8 |
| 5,874,214 A | 2/1999 | Nova et al. | |
| 5,962,834 A | 10/1999 | Markman | |
| 6,025,129 A | 2/2000 | Nova et al. | |
| 6,060,022 A | 5/2000 | Pang et al. | |

(Continued)

FOREIGN PATENT DOCUMENTS

JP  2001-188061  7/2001

(Continued)

OTHER PUBLICATIONS

New RFID Tag with More Memory, RFID Journal, Aug. 25, 2003.

(Continued)

*Primary Examiner*—John Tweel, Jr.
(74) *Attorney, Agent, or Firm*—Kilyk & Bowersox, P.L.L.C.

(57) ABSTRACT

An apparatus for associating information with a carrier and/or at least one biological reagent is provided. The apparatus can include a carrier adapted to retain at least one biological reagent and at least one non-silicon Radio Frequency Identification Tag (RFID). The RFID tag can comprise information in the form of an information pointer that can be resolved by an information pointer resolution device. The information pointer and/or resolution device can be used to access a remote system. The carrier can be configured, for example, as a microfluidic processing device or a multi-well plate. Methods and systems using the apparatus are also provided.

12 Claims, 7 Drawing Sheets

U.S. PATENT DOCUMENTS

| | | | |
|---|---|---|---|
| 6,094,137 A | 7/2000 | Rasch et al. | |
| 6,201,474 B1* | 3/2001 | Brady et al. | 340/572.8 |
| 6,206,292 B1 | 3/2001 | Robertz et al. | |
| 6,211,781 B1* | 4/2001 | McDonald | 340/572.1 |
| 6,219,137 B1 | 4/2001 | Vo-Dinh | |
| 6,259,367 B1* | 7/2001 | Klein | 340/572.1 |
| 6,297,727 B1* | 10/2001 | Nelson, Jr. | 340/572.1 |
| 6,317,028 B1 | 11/2001 | Valiulis | |
| 6,317,208 B1* | 11/2001 | Hirosawa | 356/364 |
| 6,319,668 B1 | 11/2001 | Nova et al. | |
| 6,329,139 B1 | 12/2001 | Nova et al. | |
| 6,352,854 B1 | 3/2002 | Nova et al. | |
| 6,359,444 B1* | 3/2002 | Grimes | 436/149 |
| 6,361,950 B1 | 3/2002 | Mandecki | |
| 6,372,428 B1 | 4/2002 | Nova et al. | |
| 6,376,187 B1 | 4/2002 | Mandecki | |
| 6,387,623 B1 | 5/2002 | Mandecki | |
| 6,417,010 B1 | 7/2002 | Cargill et al. | |
| 6,429,016 B1* | 8/2002 | McNeil | 436/47 |
| 6,483,434 B1* | 11/2002 | UmiKer | 340/572.1 |
| 6,520,544 B1* | 2/2003 | Mitchell et al. | 340/572.8 |
| 6,535,129 B1* | 3/2003 | Petrick | 340/572.1 |
| 6,541,211 B1 | 4/2003 | Patek et al. | |
| 6,637,473 B2 | 10/2003 | Ganz et al. | |
| 6,670,609 B2 | 12/2003 | Franzen et al. | |
| 6,677,852 B1* | 1/2004 | Landt | 340/572.1 |
| 6,699,437 B1 | 3/2004 | Astle | |
| 6,726,820 B1 | 4/2004 | Frazier | |
| 6,733,728 B1 | 5/2004 | Mimura et al. | |
| 6,734,797 B2* | 5/2004 | Shanks et al. | 340/572.4 |
| 6,889,468 B2* | 5/2005 | Bedingham et al. | 436/45 |
| 6,982,640 B2* | 1/2006 | Lindsay et al. | 340/572.1 |
| 7,061,379 B2 | 6/2006 | Chen et al. | |
| 7,091,864 B2 | 8/2006 | Veitch et al. | |
| 7,113,131 B2* | 9/2006 | Burke | 340/572.8 |
| 2001/0021356 A1 | 9/2001 | Konrad | |
| 2002/0018733 A1 | 2/2002 | Kapplein et al. | |
| 2002/0030598 A1 | 3/2002 | Dombrowski et al. | |
| 2002/0076819 A1 | 6/2002 | Bowman et al. | |
| 2002/0090320 A1 | 7/2002 | Burow et al. | |
| 2002/0094515 A1 | 7/2002 | Erlach et al. | |
| 2002/0098472 A1 | 7/2002 | Erlach et al. | |
| 2002/0098598 A1 | 7/2002 | Coffen et al. | |
| 2002/0111551 A1 | 8/2002 | Erlach et al. | |
| 2002/0114739 A1 | 8/2002 | Weigl et al. | |
| 2003/0017082 A1 | 1/2003 | van Deursen et al. | |
| 2003/0072676 A1 | 4/2003 | Fletcher-Haynes et al. | |
| 2003/0087446 A1 | 5/2003 | Eggers | |
| 2003/0087455 A1 | 5/2003 | Eggers et al. | |
| 2003/0124539 A1 | 7/2003 | Warrington et al. | |
| 2003/0151028 A1 | 8/2003 | Lawrence et al. | |
| 2003/0211012 A1 | 11/2003 | Bergstrom et al. | |
| 2003/0231986 A1 | 12/2003 | Kocher | |
| 2004/0029109 A1 | 2/2004 | Lai | |
| 2004/0094949 A1 | 5/2004 | Savagian et al. | |
| 2004/0100415 A1 | 5/2004 | Veitch et al. | |
| 2004/0101966 A1 | 5/2004 | Davis et al. | |
| 2004/0121432 A1 | 6/2004 | Klein et al. | |
| 2004/0124437 A1 | 7/2004 | Doudoumopolous | |
| 2004/0131505 A1 | 7/2004 | Koeda | |
| 2004/0136873 A1 | 7/2004 | Meier | |
| 2004/0173508 A1 | 9/2004 | Deursen et al. | |
| 2004/0173781 A1 | 9/2004 | Lawrence et al. | |
| 2004/0175515 A1 | 9/2004 | Lawrence et al. | |
| 2004/0175548 A1 | 9/2004 | Lawrence et al. | |
| 2004/0175550 A1 | 9/2004 | Lawrence et al. | |
| 2004/0202577 A1 | 10/2004 | McNeil et al. | |
| 2004/0203047 A1 | 10/2004 | Caren et al. | |
| 2006/0199196 A1 | 9/2006 | O'Banion et al. | |

FOREIGN PATENT DOCUMENTS

| | | |
|---|---|---|
| JP | 2003 289566 | 10/2003 |
| JP | 2004 061136 | 2/2004 |
| JP | 2004 093519 | 3/2004 |
| JP | 2004 166555 | 6/2004 |
| WO | WO 96/08433 A1 | 3/1996 |

OTHER PUBLICATIONS

Investor's Relationship, Vincogen web page downloaded from http://www.vincogen.com/technology.htm on Jan. 29, 2004.

Technology, Vincogen web page downloaded from http://www.vincogen.com/technology.htm on Jan. 29, 2004.

Illustration of a Microtransponder for DNA-Probe Assays, Pharmaseq web page downloaded from http://www.pharmaseq.com/illustration.html on Sep. 23, 2004.

Henke, Cliff, DNA-chip technologies—Part 3 What does the future hold?, *IVD Technology Magazine*, (1998).

* cited by examiner

SAMPLE CARRIER DEVICE INCORPORATING RADIO FREQUENCY IDENTIFICATION, AND METHOD

CROSS-REFERENCE TO RELATED APPLICATION

The present application is a Continuation-in-Part of co-pending U.S. patent application Ser. No. 10/805,093, entitled "Methods and Systems for Using RFID in Biological Field," filed Mar. 19, 2004, which is incorporated herein in its entirety by reference.

INTRODUCTION

The present teachings relate to a device, method, and system for associating information with a sample carrier, for example, of the type retaining a biological sample. During the manufacture and use of biological reagents, the reagents are typically loaded and labeled in order to keep track of them. A device, system, and method are needed that can provide for reading from and writing to a carrier including biological reagents without requiring an optical path or direct physical access to the carrier. Further, there is a need for storing greater amounts of information than that can be written on a conventional label.

SUMMARY

According to various embodiments, an apparatus for associating information with a biological reagent carrier is provided. The apparatus can comprise a carrier adapted to retain at least one biological reagent and at least one non-silicon radio-frequency identification (RFID) tag. The RFID tag can comprise a memory and an RFID antenna coupled to the carrier. The non-silicon RFID tag can be operable to be read by an RFID reader.

According to various embodiments, an apparatus for associating information with a biological reagent carrier is provided. The apparatus can comprise a carrier for retaining at least one biological reagent and at least one self-identifying integrated circuit (SIDIC). The at least one SIDIC can comprise a memory, and an output interface. The at least one SIDIC can be coupled to the carrier. Information can be stored or referenced in the memory. The memory can be immutable after a first imprinting of the information.

According to various embodiments, a system for associating information with a biological reagent carrier is provided. The system can comprise a carrier adapted to retain at least one biological reagent, an RFID tag coupled to the carrier and operable to be read by an RFID reader, an information pointer resolution device adapted to resolve an information pointer into information, and at least one biological instrument for performing operations on at least one biological reagent retained by carrier. The RFID tag can comprise identification information and the information pointer. The at least one biological instrument can use the information.

According to various embodiments, an apparatus for associating information with a biological reagent carrier is provided. The apparatus can comprise a carrier adapted to retain at least one biological reagent and at least one RFID tag coupled to the carrier. Each RFID tag of the at least one RFID tag can comprise a carrier RFID antenna and a memory. The memory can comprise information stored or referenced in the form of a log detailing a chronicle of the apparatus.

According to various embodiments, a method for associating information with a carrier is provided. The method can comprise providing a carrier adapted to retain at least one biological reagent, the carrier being coupled to a non-silicon RFID tag, and receiving from the non-silicon RFID tag, identification information associated with the carrier. The non-silicon RFID tag can be operable to be read by an RFID reader.

According to various embodiments, a method for associating information with a carrier is provided. The method can comprise providing a carrier adapted to retain a biological reagent, the carrier being coupled to an RFID tag; receiving from the RFID tag an information pointer; and resolving the information pointer into information associated with the carrier. The RFID tag can be operable to be read by an RFID reader.

Additional features and advantages of various embodiments will be set forth in part in the description that follows, and in part will be apparent from the description, or can be learned by practice of various embodiments. Other advantages of the various embodiments will be realized and attained by means of the elements and combinations exemplified in the application.

BRIEF DESCRIPTION OF THE DRAWINGS

The skilled artisan will understand that the drawings, described below, are only intended for the illustration of various embodiments. The drawings are not intended to limit the scope of the present teachings in any way. In the drawings.

DESCRIPTION OF VARIOUS EMBODIMENTS

Figure 1:
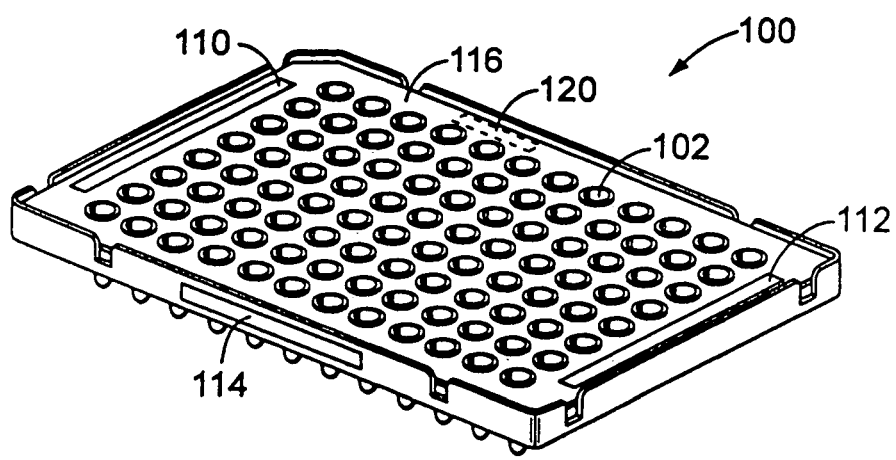
FIG. 1 illustrates a perspective view from above a reaction plate having a plurality of reaction wells and various exemplary locations for RFID tags according to various embodiments.

Reference will now be made in detail to some embodiments, examples of which are illustrated in the accompanying drawings. Wherever possible, the same reference numbers are used throughout the drawings to refer to the same or like parts.

According to various embodiments, Radio Frequency Identification ("RFID") provides a convenient mechanism for identifying and detecting sample carriers using wireless electromagnetic signals. A basic RFID system has at least one RFID reader and at least one RFID tag. Typically, RFID readers can include a coil or antenna and circuitry to transmit and receive signals with the coil or antenna. An RFID tag also includes a coil or antenna and some information that can be read by an RFID reader.

According to various embodiments, the RFID reader antenna can generate an electromagnetic field, thereby transferring energy to the tag. Depending on the design of the tag, a portion of the energy transferred to the tag will be reflected to the reader so as to provide information about the tag back to the reader. Some RFID systems can be used to read and optionally write information to and from the RFID tag. RFID readers can generate signals spanning distances from less than one inch to more than 100 feet depending on frequency and power of the signals generated at the RFID reader antenna.

According to various embodiments, the RFID tags can be categorized as either active or passive. Active RFID tags are powered by an internal battery and are typically read/write, i.e., tag data can be rewritten and/or modified. An active tag's memory size varies according to application requirements; some systems operate with up to 1 MB of memory.

According to various embodiments, the passive RFID tags can operate without a separate external power and obtain operating power generated from the reader. Passive tags are consequently typically lighter than active tags, less expensive, and offer a long operational lifetime. Passive tags typically have shorter read ranges than active tags and require a higher-powered reader. Read-only tags are typically passive and can be programmed with a unique set of information (usually 32 to 128 bits) that is typically predetermined at the time of manufacture of the tag. It is understood that passive read/write tags can also be employed consistent with the present teachings.

The term "RFID tag" as used herein can, in some embodiments, refer to either an active or passive RFID tag that contains information. The RFID tag can be read only or read/write, and the information associated with the RFID tag can be hard-coded into the RFID tag at the time of manufacture or at some later time, or the RFID tag can contain information that is written to the RFID tag throughout its lifetime. The RFID tag can be coated with at least one layer of material, for example, a protective polymer or a glass, including polystyrene, heavy metal-free glass, plastic, ceramic, and can be coated with more than one layers of this and other materials. For example, it may be coated with a ceramic or glass, which is then coated with or linked to the carrier material. Alternatively, the glass or ceramic or other coating can serve as the carrier. Radio frequencies can be used to communicate with the RFID tag. According to various embodiments, other frequencies or lasers can be used to communicate with the RFID tag, as long as the selected frequency or laser does not interfere with the interactions of the molecules or biological particles of interest. Thus, information in the form of data points can be stored or referenced in, and retrieved from the data storage device by application of a selected electromagnetic radiation frequency.

The term "non-silicon RFID tag" as used herein can, in some embodiments, refer to an RFID tag comprising organic material and/or a polymer RFID tag comprising a metal dopant, and a polymeric material. Exemplary non-silicon RFID tags are, described in U.S. Published Patent Applications Nos. US 2003/0151028 A1, US 2004/0094949 A1, US 2004/0175550 A1, US 2004/0175515 A1, and US 2004/0175548 A1, all of which are incorporated in their entireties by reference.

The term "RFID reader" as used herein can, in some embodiments, refer to RFID devices that can read information from and/or write information into an RFID tag.

The term "carrier" as used herein can, in some embodiments, refer to a structure for directly or indirectly supporting a biological reagent. Examples of carriers include reaction plates, tubes, tube carriers, surface plasmon resonance arrays, slides, conical low-volume tubes, microfluidic cards, microarray cartridges, microarrays, sample preparation devices, assay preparation devices, electrophoretic type device, electroosmotic type devices, immunoassays, combinatorial libraries, molecular libraries, phage display libraries, DNA libraries, DNA fingerprinting devices, SNP detection devices, vacuum containers, and other types of containers for supporting biological reagents. The carrier can be a multi-well tray including, for example, 4, 12, 24, 48, 96, 192, 384, 768, 1536, 3072, 6144, 12288, or more wells or sample retainment regions. The carrier can be a carrier as described, for example, in U.S. patent application Ser. No. 10/944,691, filed Sep. 17, 2004, which is incorporated herein in its entirety by reference. The carrier can retain a fluid, if the carrier can be utilized to transfer, contain, encompass, or otherwise hold, permanently or temporarily, a fluid. The carrier material can comprise any materials used in chemical and biochemical synthesis. The carrier material can comprise polymeric materials that are compatible with chemical and biological syntheses and assays, and include glasses, silicates, celluloses, polystyrenes, polysaccharides, sand, and synthetic resins and polymers, including acrylamides, particularly cross-linked polymers, cotton, and other such materials. The carrier material can be in the form of particles or can be continuous in design, such as a test tube or microtiter plate or the like.

The term "biological reagent" as used herein can, in some embodiments, refer to a biological material used for various biological analyses such as detecting, examining, and/or measuring information from biological samples. Biological analyses can include reactions such as polymerase chain reaction (PCR), ligase chain reaction, antibody binding reaction, oligonucleotide ligation assays, and hybridization assays. Examples of biological reagents include nucleic acids, primers, probes, other biological reagents, biological samples, environmental samples, other types of samples, proteins, carbohydrates, lipids, bodily fluids, biopsy, cheek swab, other patient samples, a biological particle, and combinations there of, which can be used in performing various biological assays. "Nucleic acid" as used herein refers to nucleotides, oligonucleotides, DNA, RNA, PNA, and the like, as these terms are understood by those skilled in the art of genomics.

The term "coupling" as used herein can, in some embodiments, comprise two items being in physical contact with each other, directly or indirectly, or in proximity with each other. For example, a biological reagent can be in physical contact with the carrier, that in turn can be in physical contact or in the proximity of the RFID tag. The carrier can be on a surface of the RFID tag and the molecules and biological particles can be in physical contact with the carrier. An RFID tag, a polymer RFID tag, printed on a carrier is said to be coupled to that carrier. Coupling can be effected by placing the RFID tag on or in the carrier material or in a solution that is in contact with the carrier material or by linking the RFID tag, either by direct or indirect covalent or non-covalent interactions, chemical linkages or by other interactions, to the carrier. For example, such contact can be effected chemically, by chemically coupling the RFID tag to the carrier, or physically by coating the RFID tag with the carrier material or another material, by physically inserting or encasing the RFID tag in the carrier material, by placing the RFID tag onto the carrier or by printing the RFID tag on the carrier material or by any other means by which the RFID tag can be placed in contact with or in proximity to the carrier material. Coupling can comprise affixing, embedding, attaching, printing, bonding, coating, otherwise coupling, or any combination thereof.

The term "information" as used herein can, in some embodiments, refer to data that can be stored or referenced electronically in the RFID tag. The information can be retrieved from a memory in/on the RFID tag itself. An information pointer resolution device can retrieve the information. The information pointer resolution device can use the identification to retrieve apparatus, biological reagent, and/or carrier information. The information pointer resolution device can use the information retrieved from the memory in/on the RFID tag itself to retrieve apparatus, biological reagent, and/or carrier information. The information can be machine readable and/or human readable data. Information can be utilized for processing the biological reagent, a reader, carrier, a biological instrument capable of utilizing the carrier, or any combination thereof. Information used herein comprises all types of information described herein.

The term "identification information" as used herein can, in some embodiments, refer to information on an RFID tag that can be used to uniquely identify a particular carrier or biological reagent or to distinguish the carrier or biological reagent from other carriers or biological reagents. For example, identification can relate a particular assay prepared for a particular customer.

The term "supplemental information" as used herein can, in some embodiments, refer to descriptive information about a carrier or its contents, including certain biological reagents. Examples of supplemental information include nucleic acid sequence information, annotated information regarding experiments performed with various biological reagents, a material safety data sheet, batch or log information, information regarding experiments scheduled to be performed, assays to be performed, permission information, access control information, and a list of biological instruments certified or approved to perform a desired assay using the carrier.

The term "rights information" as used herein can, in some embodiments, refer to authorization information for carriers or biological reagents, such as information regarding whether a particular licensee has a valid license to use a particular carrier or biological reagent, including a number of times the licensee is permitted to use the particular carrier or biological reagent in a particular assay. Rights information can also include validation information regarding whether a particular carrier or biological reagent has been subject to a recall or has otherwise become unsuitable or unauthorized for use.

The term "genealogy information" as used herein can, in some embodiments, refer to information regarding the derivation of a biological reagent, including for example an identification of an original sample from which it was derived or the number of generations removed it is from an original sample.

The term "traveler information" as used herein can, in some embodiments, refer to information regarding a carrier or a biological reagent contained as operations are performed on that carrier or biological reagent for example during manufature of the biological reagent or while an assay is being performed on the biological reagent.

The term "log" or "data log," as used herein can, in some embodiments, refer to a computerized record. The log can be a file. The log does not have to be written-to linearly or sequentially in an implied, implicit, or explicit order. The log can be organized in a computer data-structure well known in the art. The mechanism, means, or device to make a log append-only can comprise hardware, software, or wetware. The log can comprise one or more records in a database. The log can be utilized to, for example, track a carrier, test or assay, compile and catalog the results of an assay, check on stations that have processed the carrier, or notify a user of test results. The log can be utilized to see, for example, what carrier is presently disposed in what instrument.

The term "log information" as used herein can, in some embodiments, refer to information stored or referenced in a log. The log can comprise information about the biological reagent. The log can comprise information about at least one of an initial patient sample, a patient biography, a patient medical history, a history of apparatus transfers, a chain of custody for the apparatus, a history of purifications, a history of reactions performed using the biological reagent, a user's notes, a born-on date, a manufacturing date, an expiration date, a list of user's who have manipulated the apparatus, an experiment performed with a biological reagent, a result of an experiment performed with a biological reagent, or a combination thereof. The log information can comprise assays, assay results, conditions of a biological instrument utilizing the carrier or biological reagent, a user access of the carrier or biological reagent, and other carrier or biological reagent handling information.

According to various embodiments, an apparatus for associating information with a biological reagent carrier is provided. The apparatus can comprise a carrier adapted to retain at least one biological reagent and at least one non-silicon radio-frequency identification tag. The non-silicon RFID tag can comprise a memory and an RFID antenna coupled to the carrier. The non-silicon RFID tag can be operable to be read by an RFID reader.

According to various embodiments, the at least one non-silicon RFID tag can comprise at least one organic RFID tag. The at least one non-silicon RFID tag can comprise at least one polymer RFID tag comprising a metal dopant and a polymeric material. The at least one non-silicon RFID tag can comprise a read-only memory, a write-once memory, or a read-write memory. A read-only memory can be read one or more times, but cannot be written to; a write-once memory can be written to once and only once and read one or more times; and a read-write memory can be read and written to one or more times.

According to various embodiments, the carrier can comprise at least one of a microarray, a surface plasmon resonance array, a reaction plate, a tube, a tube carrier for holding a plurality of tubes, a microfluidic card device, a multi-well plate, or a combination thereof. The carrier RFID antenna can be embedded in an interior portion of the carrier during a carrier manufacturing process. The carrier RFID antenna can be adhesively applied or otherwise coupled to at least part of an exterior portion of the carrier.

According to various embodiments, the carrier can comprise at least one biological reagent retained thereby. The at least one non-silicon RFID tag can comprise, stored or referenced therein, at least one of identifying information pertaining to the at least one biological reagent, supplemental information pertaining to the at least one biological reagent, rights information pertaining to the at least one biological reagent, license information pertaining to the at least one biological reagent, instrument operation information pertaining to the at least one biological reagent, identification information pertaining to the apparatus, supplemental information pertaining to apparatus, rights information pertaining to the apparatus, instrument operation information pertaining to the apparatus, license information pertaining to the apparatus, or a combination thereof. The at least one non-silicon RFID tag can comprise a memory adapted to store or reference at least 64 bytes of information, at least 1 kilobyte of information, at least 4 kilobytes of information, at least 64 kilobytes of information, at least 512 kilobytes of information, at about 5 megabytes of information, or more.

According to various embodiments, a system can comprise an apparatus and an instrument RFID reader for reading the at least one non-silicon RFID tag, and at least one output interface coupled to the instrument RFID reader. The RFID reader can be adapted to output information from the at least one non-silicon RFID tag. The instrument RFID reader can comprise a non-transparent enclosure that can substantially prevent optical scanning of a barcode on an object positioned within the instrument RFID reader. The at least one output interface can comprise a wired network port, a wireless network port, a computer bus, a universal serial bus port, a serial port, a parallel port, an IEEE-1384 port, an infrared port, a transmitter, an optical fiber, a line-of-sight transmitter receiver pair, or a combination thereof. In some embodiments, the at least one output interface can comprise means well known in the art.

According to various embodiments, the tag can comprise a power source adapted to convert blood pressure changes from a mammal into electrical energy to energize the tag. In some embodiments, an appropriate transducer can be used by the power source. In some embodiments, the power source can comprise a capacitive device and/or a strain-type device. The tag can comprise a power source comprising an electric transducer to energize the tag. The electrical energy can be utilized to energize the tag, when the tag is not disposed in a tag reader. The power source can power a diagnostic circuit, for example, to test a glucose monitor, a blood chemistry monitor, a blood pressure monitor, a blood-oxygen monitor, a cardiac monitor, a respiratory monitor, or a gastronomic monitor. The tag can be, for example, an RFID tag, a non-silicon RFID tag, or an SIDIC tag.

According to various embodiments, the tag can comprise a power source, for example, a battery or a power source adapted to convert pressure changes, for example, blood pressure changes, into a voltage and a current. The power source can comprise, for example, a flexible member. The tag can be fixed to an inner wall of a body fluid vessel, for example, within a large artery or a main transport artery, for example, in the carotid artery. In some embodiments, the power source can comprise a strain-type device, for example, a piezo-electric device. The power source can comprise a sealed vessel. In some embodiments, the power source can comprise a capacitive-type device, for example, that comprises a transducer adapted to convert pressure changes into an electrical voltage change. Information about physical, chemical, and/or biological events or changes can be recorded into a memory of the tag. The tag can be read by a tag reader.

According to various embodiments, various devices and methods that can incorporate or use a write-once memory, SIDIC, or RFID, tag or system, and/or a method as described herein, can include, for example, the microdevices and nanodevices and methods described in U.S. Patent Application Publication No. US 2002/0111551 A1 published Aug. 15, 2002, the micro or nanodevices and methods described in U.S. Patent Application Publication No. U.S. 2002/0098472A1 published Jul. 25, 2002, the micro or nanodevices and methods described in U.S. Patent Application Publication No. 2002/0094515 A1 published Jul. 18, 2002, and the nanoprobes and methods described in U.S. Pat. No. 6,219,137 B1 issued Apr. 17, 2001, all of which are herein incorporated in their entireties by reference.

In an exemplary embodiment, the radio transmitter and power supply described in U.S. Patent Application Publication No. 2002/0111551 A1 can be replaced with a write-once memory, an SIDIC, or on RFID, tag as described herein. The device can then be introduced into an animal body, for example, into a fluid stream in a mammalian body, and the methods of reading and recording information as described herein can be performed to read and write information about the body.

According to various embodiments, an apparatus for associating information with a biological reagent carrier is provided. The apparatus can comprise a carrier adapted to retain at least one biological reagent and at least one self-identifying integrated circuit (SIDIC). The at least one SIDIC can comprise a memory and an output interface. The at least one SIDIC can be coupled to the carrier. Information can be stored or referenced in the memory. The memory can be immutable after a first imprinting of the information.

According to various embodiments, the apparatus can further comprise a laser adapted for laser ablation of the memory. The carrier can comprise at least one of a microarray, a surface plasmon resonance array, a reaction plate, a tube, a tube carrier for holding a plurality of tubes, a microfluidic card device, a multi-well plate, or a combination thereof. The output interface can comprise a remote transmission of the information. The apparatus can comprise a power-supply adapted to convert a transmission of electromagnetic energy to an electrical current for powering the SIDIC.

An exemplary self-identifying integrated circuit (SIDIC) is described in U.S. Patent Application Publication No. US 2004/0124437, incorporated herein in its entirety by reference. The SIDIC can be used to identify carriers and/or biological reagents stored therein. The SIDIC can be passive or active. The SIDIC can be powered using a laser. The SIDIC can be powered using an infrared beam. The SIDIC can be immutable. The circuitry to store the unique identification code can be fabricated on a microscopic scale such as by a direct-write laser forward transfer of material process or by a laser ablation of select material process. The identification storage means can be disposed on a package substrate or on an integrated circuit die and can be permanently encased within the integrated circuit package so as to be protected from alteration by external means.

According to various embodiments, a system for associating information with a biological reagent carrier is provided. The apparatus can comprise a carrier adapted to retain at least one biological reagent, an RFID tag coupled to the carrier and operable to read an RFID reader, and an information pointer resolution device adapted to resolve an information pointer into information. The system can comprise at least one biological instrument for performing operations on at least one biological reagent retained by the carrier. The RFID tag comprises identification information and the information pointer. The at least one biological instrument can utilize the information.

According to various embodiments, the RFID tag can comprise identification information and the identification information can comprise an information pointer. An information pointer resolution device can utilize the identification information to perform off-carrier information retrieval from a database, for example, a database resident in a computer comprising the information pointer resolution device, a database in intra-network communication with the information pointer resolution device, or a database in inter-network communication with the information pointer resolution device. The information pointer resolution device can be adapted to perform multiple and/or recursive lookups on retrieved information.

According to various embodiments, the information pointer can comprise a Uniform Resource Indicator (URI), a Uniform Resource Name (URN), a Uniform Resource Locator (URL), a network service address, an internet protocol (IP) address and an IP port, an inter-process communication (IPC) identifier, or a combination thereof. Further clarification of a URI, a URN and a URL can be obtained at http://www.w3.org/TR/uri-clarification. The RFID tag can comprise permission control information for a remote system to obtain access to the apparatus. The RFID tag can comprise permission control information for the pointer resolution device to obtain access to a remote system. The permission control information can comprise at least one of identification information, authentication information, location information, security classification information, reliability classification information,-or any combination thereof.

According to various embodiments, the information can comprise at least one of identification information pertaining to at least one biological reagent, supplemental information pertaining to at least one biological reagent, rights information pertaining to at least one biological reagent, license information pertaining to at least one biological reagent, biological instrument operation information pertaining to at least one biological reagent, identification information for the carrier, supplemental information for the carrier, rights information for the carrier, biological instrument operation information for the carrier, license information for the carrier, or a combination thereof. The information can comprise biological instrument operation information for defining an operation of the at least one biological instrument.

According to various embodiments, the information pointer resolution device can be capable of providing an identity indication of the biological reagent based on the identification information. The pointer resolution device can comprise a wired network port, a wireless network port, a computer bus, a universal serial bus port, a serial port, a parallel port, an IEEE-1384 port, an infrared port, a transmitter, an optical pathway, or any combination thereof. The information pointer resolution device can be adapted to access a data log adapted to store or reference information output by the apparatus. The data log can be keyed by the identification information.

According to various embodiments, the system can comprise an automated system adapted to transport the carrier to at least one of the at least one biological instrument or the RFID reader. The system can comprise a biological instrument controller coupled to the biological instrument and the RFID reader. The biological instrument controller can comprise instrument hardware, instrument firmware, and instrument data collection software. The biological instrument controller can comprise a general purpose computer. The general purpose computer can be coupled to the biological instrument via a data network connection that is operable to carry the instrument operation information back and forth between the general purpose computer and the biological instrument. The biological instrument operation information can comprise parameters for defining operation of the instrument and/or instrument data collection software.

According to various embodiments, an apparatus for associating information with a biological reagent is provided. The apparatus can comprise a carrier adapted to retain at least one biological reagent and at least one RFID tag coupled to the carrier. The RFID tag can comprise an RFID antenna and a memory. The memory can comprise information stored or referenced in the form of a log detailing a chronicle of the apparatus.

According to various embodiments, the carrier can be adapted to perform an assay on a sample comprising a bodily fluid. At least one biological reagent can be retained by the carrier. The log can comprise results of an assay performed using the at least one biological reagent. The assay can comprise results pertaining to, for example, glucose monitoring, medical diagnostics, proteins indicating a heart attack, or enzymatic detection. The at least one biological reagent can comprise a nucleic acid. The log can comprise information pertaining to a nucleic acid sequence.

If an append-only log is provided, it can comprise a log that cannot be overwritten or reused. The log can be made to only be appended or added to. The log can be "append-only" in its use or appearance for a subset of users or clients of the log. A subset of users and/or clients of the log can be allowed to perform operations beyond reading or appending to the log. The log can be an append-only log.

According to various embodiments, a log can be implemented as a file, a plurality of files, a record in a database, a plurality of records in a database, or other database structure well known in the art. The log can be implemented using a relational database management system.

According to various embodiments, the carrier can comprise a substrate including a surface, and a separation channel formed in or on the surface. A sample comprising an analyte can be disposed in the separation channel. The RFID tag can comprise a supplemental memory. Information pertaining to the analytes can be stored or referenced in the supplemental memory. The information can comprise one or more biological characteristics of the analytes and/or the sample.

According to various embodiments, the apparatus can comprise one or more electrodes. Each electrode can be capable of being connected to a power source, and the one or more electrodes can be disposed with respect to the separation channel for generating one or more electrical fields along at least a portion thereof. The carrier can comprise a plurality of separation channels and the separation channels can be non-intersecting.

According to various embodiments, a method for associating information with a carrier is provided. The method can comprise providing a carrier adapted to retain at least one biological reagent, the carrier being coupled to a non-silicon RFID tag, and receiving from the non-silicon RFID tag, identification information associated with the biological reagent. The non-silicon RFID tag can be read by an RFID reader. The non-silicon RFID tag can comprise reagent information stored therein pertaining to at least one biological reagent.

According to various embodiments, the method can comprise receiving from the non-silicon RFID tag reagent information. The method can comprise tracking the carrier as the carrier undergoes a reagent manufacturing process. The method can comprise obtaining real-time physical location coordinates associated with the biological reagent. The reagent information can comprise real-time physical information. Obtaining the real-time physical location coordinates can comprise receiving RFID triangulation parameters from a plurality of triangulation RFID readers proximate to the non-silicon RFID tag and/or receiving GPS coordinates from a GPS receiver physically coupled to the carrier. The method can comprise maintaining a threshold inventory quantity of units of the biological reagent based on a count of the carriers established by reading the non-silicon RFID tag associated with the units.

According to various embodiments, the non-silicon RFID tag used in any of the methods described herein can comprise at least one organic RFID tag and/or at least one polymer RFID tag comprising a metal dopant in a polymer, for example, as described herein.

According to various embodiments, a method for associating information with a carrier is provided. The method can comprise: providing a carrier adapted to retain at least one biological reagent, the carrier being coupled to an RFID tag; receiving from the RFID tag, an information pointer; and resolving the information pointer into information associated with the carrier. The RFID tag can be operable to be read by an RFID reader.

According to various embodiments, the method can comprise storing in the RFID tag permission control information pertaining to the carrier or at least one biological reagent. The permission control information can comprise at least one of identification information, authentication information, location information, security classification information, reliability classification information, or any combination thereof. The permission control information can comprise regulatory agency standards data and/or compliance information.

According to various embodiments, the carrier can retain at least one biological reagent. The method can comprise storing information pertaining to the biological reagent by writing a chronicle using the information pointer. The information can be stored or referenced while or after the at least one biological reagent is utilized in a biological assay. The method can comprise storing traveler and/or chain of custody information regarding the at least one biological reagent and/or the carrier. The method can comprise writing and/or reading genealogical information pertaining to the at least one biological reagent.

According to various embodiments, the information can comprise annotated reagent information regarding past experiments performed with the at least one biological reagent. The information can comprise material safety data sheet (MSDS) information. The information can comprise work order number information. The information can comprise customer identifier information. The information can comprise customs service information. The customs service information can comprise country of origin information. The information can comprise lot number information. The information can comprise batch number information. The information can comprise gene expression results, DNA fingerprinting results, or assay results. The information can comprise information about a SNP, a genetic sequence, or a sequence associated with a primer and/or a probe. The information can be used in various reactions, for example, for PCR, for sequencing, for re-sequencing, for fingerprinting, for oligonucleotides useful in an isothermal detection assay, or for probes in a hybridization array.

The method can comprise receiving, from the information, rights information associated with the biological reagent. The method can comprise authorizing under terms of a license, use of the at least one biological reagent and/or the carrier in a biological assay. The method can further comprise receiving license identifier information from the information, authenticating the license identifier information, and based on the authenticated license identifier information, permitting the performance of at least one licensed activity in connection with the carrier and/or the at least one biological reagent. The at least one licensed activity can comprise a biological assay performed on a separately licensed instrument. The license identifier information can comprise a digital signature.

According to various embodiments, the method can comprise validating integrity of the carrier and/or the at least one biological reagent for use in connection with a specific biological assay. Validating the integrity of the biological reagent can comprise employing at least a portion of the rights information in a recall-list lookup operation to determine whether the biological reagent has been subject to a recall.

According to various embodiments, the method can receive, from the information, instrument operation information associated with the biological reagent. The instrument operation information can comprise parameters for controlling software on a biological instrument coupled to the carrier. The instrument operation information can comprise at least one sequence of operations to be performed on a biological instrument coupled to the carrier. The instrument operation information can comprise at least one set of conditions for changing states within a software-implemented state machine in a biological instrument coupled to the carrier.

According to various embodiments, the method can comprise coupling the carrier to an automation system, a controller, or a network coupled to an automation system. The method can comprise accessing an external database or an URI through the coupling. The information stored or referenced in the RFID tag can comprise at least one of a patient's information, a doctor's information, a manufacturer's information, a referrer's information, or a combination thereof. The assay device can comprise a microarray comprising a plurality of detections sites. The assay device can comprise a human genome microarray. The information can comprise detection results for a plurality of detection sites. The detection results can be used to form results of allele matching, for example, allele matching of a human genome.

According to various embodiments, a method is provided comprising providing a carrier adapted to retain at least one biological reagent, an RFID tag coupled to the carrier, and at least one biological reagent retained by the carrier. The RFID tag can comprise an RFID antenna and an RFID memory. The method can comprise performing an assay on the biological sample, detecting the assay results, and storing information in the memory about the assay results.

Figure 7:
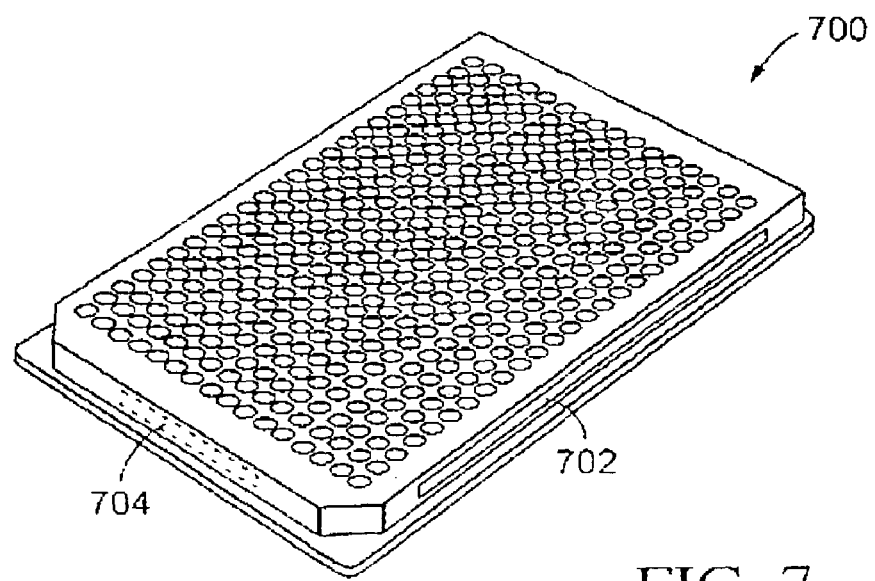
FIG. 7 illustrates another exemplary embodiment of a reaction plate in connection with various exemplary locations for RFID tags according to various embodiments.

With reference now to the drawings, FIG. 1 illustrates a perspective view from above of a reaction plate 100 having a plurality of reaction wells 102 and exemplary locations 110, 112, 114, and 120 for RFID tags. It is understood that exemplary location 110 for the RFID tag, for example, can be positioned on the exterior of the reaction plate 100 in any convenient location that will permit appropriate antenna geometry and accommodate the necessary passive or active RFID circuitry necessary for proper operation of the RFID tag. For example, RFID tags 110 and 112 are shown as boxes placed in the margins of the reaction plate 110 on an upper surface 116 of the reaction plate 100. Adhesive application or otherwise coupling of an RFID tag to the surface 116 of the reaction plate 100 can advantageously permit standard consumables, such as a reaction plate 100 to be manufactured and/or acquired independently from the RFID tags. Alternatively, RFID tag 120, illustrated in broken lines, can be embedded or otherwise coupled in the reaction plate 100, for example during a plastic injection molding or a blow molding manufacturing process. Trays and microcards are typically constructed of polypropylene so as to be compatible with PCR thermal cycling. Other carriers that provide transport containers as opposed to reaction containers can be made of harder plastics e.g. Lexan ® (General Electric). FIG. 1 illustrates a 96-well reaction plate. As illustrated in FIG. 7, other reaction plates such as 386-well reaction plates are contemplated by the present teachings.

Figure 2:
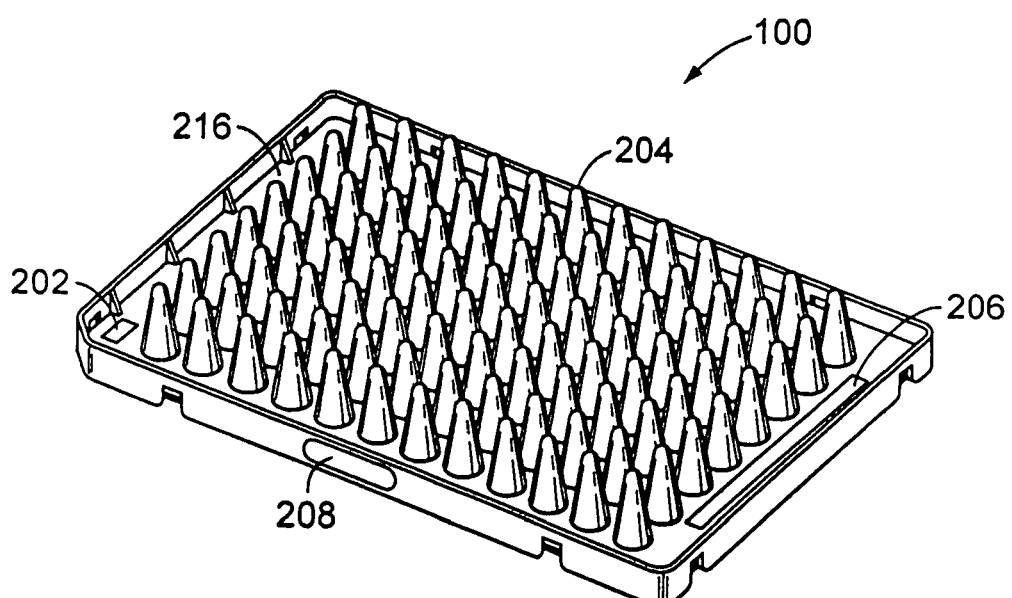
FIG. 2 illustrates a perspective view from beneath a reaction plate having a plurality of reaction wells and various exemplary locations for RFID tags according to various embodiments.

FIG. 2 illustrates an underside perspective view of the reaction plate 100 showing the undersides 204 of a plurality of reaction wells and at least one RFID tag 202 affixed to an underside portion of the reaction plate. As shown in FIG. 2, the RFID tags can be placed on the underside of the carrier as shown in connection with RFID tags 202 and 206, which are shown to be applied to the surface 216 of the reaction plate 100. Alternatively, an RFID tag 208 can be applied to a side surface of the reaction plate 100. As set forth in connection with FIG. 1, in various embodiments, the RFID tags can, for example, be adhesively applied or otherwise coupled to consumables, such as on the reaction plate 100. However, the RFID tags can also be embedded or otherwise coupled in the body of the consumables, for example during a plastic injection molding or a blow molding manufacturing process. To facilitate a transition from barcodes to RFID, both barcodes (not shown) and RFID tags can be present on consumables consistent with the present teachings, such as the reaction plate 100.

According to various embodiments, the reaction plates contain biological reagents such as nucleic acid materials, primers, and probes, which are used in connection with various biological assays to determine, for example a genetic sequence of a particular sample. In various embodiments, separate RFID tags on the plate are associated with groups of wells within the reaction plate. In other embodiments, an RFID tag is associated with a single well in the reaction plate 100. In other embodiments, a single RFID tag is associated with the entire reaction plate, with the RFID tag containing information regarding each of the wells and the contents and history of the contents of each of the well. In such embodiments, a read/write RFID tag containing a substantial amount of memory can include information, for example, biological reagent, identification, supplemental, and/or rights information about the contents of the wells 102 (of FIG. 1).

Figure 3:
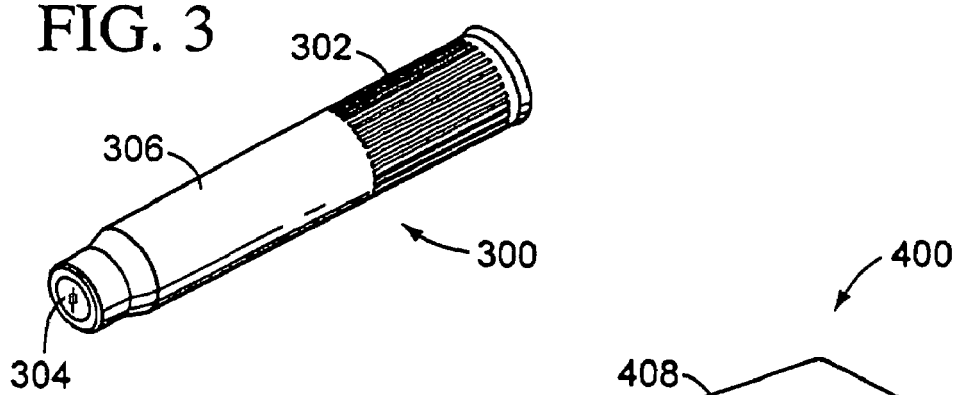
FIG. 3 illustrates a tube in connection with various exemplary locations for RFID tags according to various embodiments.

FIG. 3 illustrates a tube 300 having RFID tags positioned in alternative configurations on the tube 300. The tubes can have a conical internal volume to provide pipette access to small volumes. In various embodiments, the tubes bear both human-readable and/or machine-readable indicia regarding the contents of the tube and/or barcodes in addition to an RFID tag. In various embodiments, the RFID tag is adhesively applied or otherwise coupled to outer surface 306 of the tube 300 in connection with a label for providing optically-accessible indicia. In various embodiments, RFID tags are provided in the form of printable labels containing an RFID tag integral with the label. The RFID tags can be printed onto a carrier itself, without using an intermediary backing for the RFID tag. A printed RFID tag does not have to be visible to the eye. The RFID tags can also be affixed to, embedded in, or otherwise coupled to a bottom portion of the tube, as shown by RFID tag 304 in FIG. 3. Tubes can store nucleic acids for assays designed for a particular customer or for a particular assay.

Figure 4:
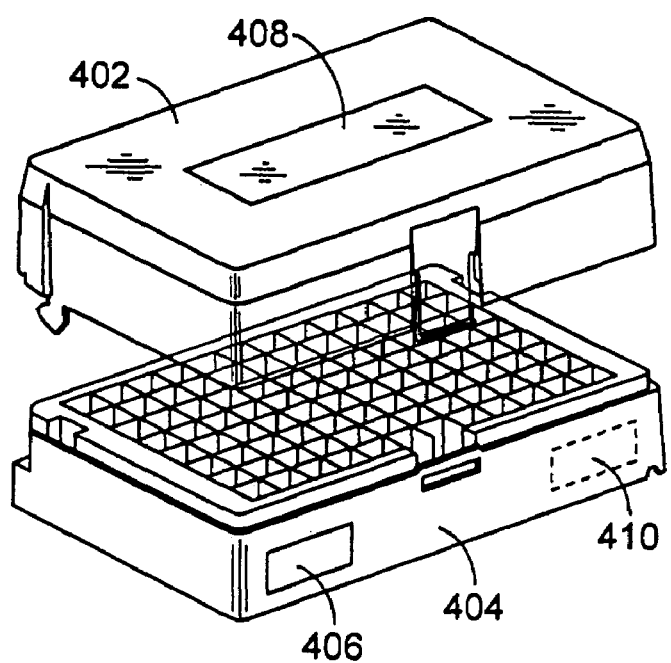
FIG. 4 illustrates an embodiment of an empty tube carrier in connection with various exemplary locations for RFID tags according to various embodiments.

FIG. 4 illustrates an embodiment of an empty tube carrier having an RFID positioned at various locations. Tube carriers such as tube carrier 400 are advantageously used to organize and transport a plurality of the tubes 300 containing biological materials. Lid 402 and tube carrier base 404 are used to protect and/or to store the tubes 300 during manufacturing, storage, transportation, and usage phases of the lifecycle of the biological materials supported by the tubes 300. In various embodiments, RFID tags in or on the tubes contain information regarding nucleic acid samples, primers, or probes contained in each of the tubes. In such embodiments, information regarding the genetic sequences of the nucleic acids, for example, are stored or referenced in the RFID tags. Further, annotated information regarding the biological reagents can be stored in the RFID tags, for example, information regarding results of experiments already performed with the biological reagents.

According to various embodiments, no read/write RFID tag is directly coupled to a particular tube. Rather, the tube bears a simplified RFID tag or optical indicia that provides, for example, row and column information for the tube's position in the tube carrier 400. Then, for example, information regarding the contents of tubes can be stored or referenced in a more complex RFID tag that is be affixed to, embedded in, or otherwise coupled to the tube carrier 400, either at the lid 402 or at the carrier base 404. Alternatively, additional information can be stored or referenced on a CDROM or other removable medium and associated with each tube, for example, based on a unique identifier on the RFID tag associated with the tube or tube carrier. The additional information can also be provided in an encrypted on-line database, as further set forth in connection with FIG. 11.

Exemplary RFID tag positions are illustrated in connection with FIG. 4. An RFID tag 408 can be applied to a surface of the lid 402. Alternatively, an RFID tag 406 can be applied to a surface of the tube carrier base 404. Still alternatively, the RFID tag 410 can be embedded into or otherwise coupled to a portion of the tube carrier 400 during a manufacturing process of the tube carrier 400. It is understood that the positions of the RFID tags 406, 408, and 410 are exemplary and not inclusive and that a single or multiple RFID tags can be affixed to, embedded in, or otherwise coupled to various portions of the tube carrier 400 without departing from the present teachings.

Figure 5:
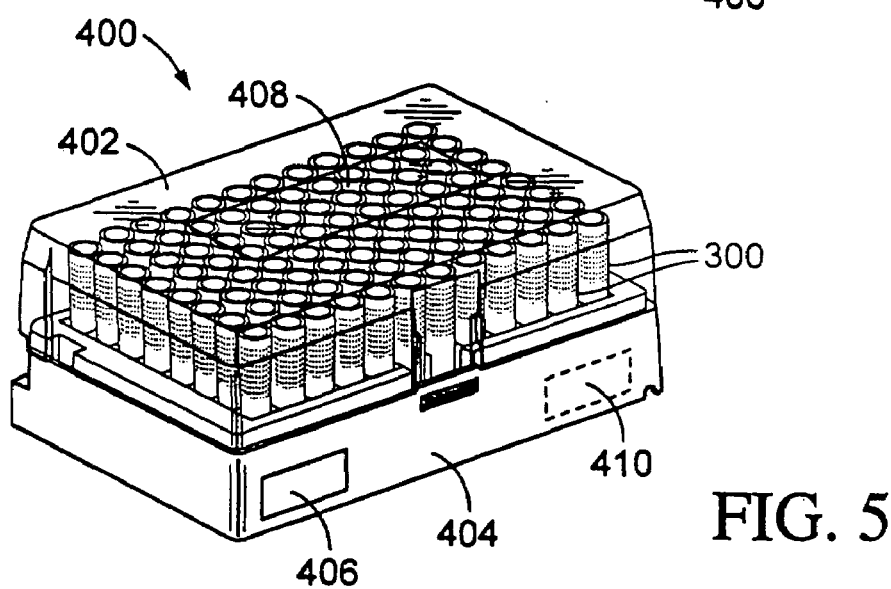
FIG. 5 illustrates a tube carrier containing a plurality of tubes in connection with various exemplary locations for RFID tags according to various embodiments.

FIG. 5 illustrates a tube carrier containing a plurality of tubes having associated individual RFID tags and at least one RFID tag on the tube carrier. In various embodiments, as shown in FIG. 5, tube carriers, such as the tube carrier 400 can contain a plurality of the tubes 300. In these various embodiments information regarding the contents of the tubes, including, for example nucleic acid sequence information, and other annotated information is stored or referenced in an RFID tag either affixed to, embedded in, or otherwise coupled to each of the tubes 300 or in an RFID tag that is affixed to, embedded in, or otherwise coupled to the tube carrier 400.

According to various embodiments, the tube carrier 400 can contain a simplified RFID tag containing only an identifier number, which is cross-referenced to a table that contains information on the contents of the particular tubes 300 in the particular tube carrier 400. In various embodiments, the lookup table information is provided on removable, machine-readable media, such as CDROM. In various other embodiments, the lookup table information is provided in the form of a network-accessible, on-line database. In various ones of these embodiments, the lookup table information is encrypted either in an off-line CDROM-type form or in an on-line form.

According to various embodiments, authentication and/or decryption information can be stored or referenced in the RFID tag or tags on or in the tubes 300 and/or the tube carrier 400. It is understood that any type of digital authentication and/or cryptography system can be employed to provide access to and decryption for the on-line or off-line information associated with the biological contents of the carriers without departing from the scope of the present teachings.

Figure 6:
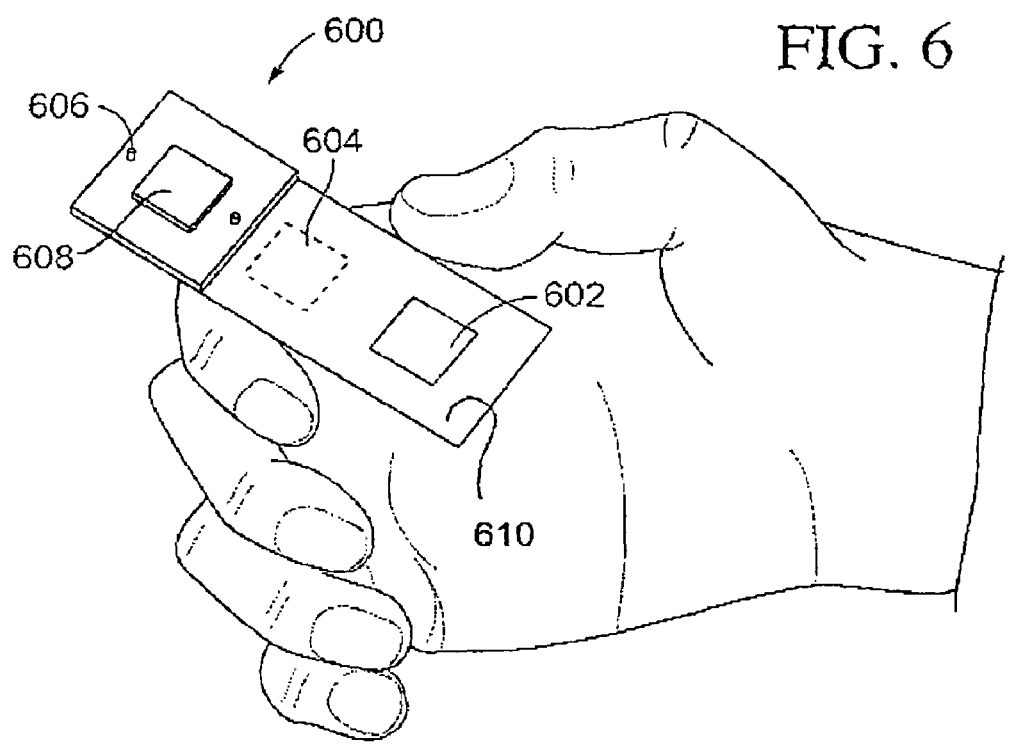
FIG. 6 illustrates an exemplary embodiment of a surface plasmon resonance (SPR) array in connection with various exemplary locations for RFID tags according to various embodiments.

FIG. 6 illustrates an exemplary embodiment of an SPR array 600 with exemplary RFID tags 604 and 602. The SPR array 600 contains ports 606 that are used to inject a biological reagent into the SPR array. In various embodiments, RFID tags 602 and 604 facilitate the association of information with biological reagents used in connection with the SPR array 600. For example, read/write RFID tag 602 can contain information regarding the biological sample injected into the SPR array. The RFID tag 602 can also be written to by an instrument that is used to detect the results of an assay conducted on the biological reagent that is injected into the SPR array. The RFID tag can further store or reference information regarding locations and patterns of particular nucleic acid spots in the SPR array.

As described above in connection with other consumables, the RFID tags 602 and 604 can be affixed to an outer surface of the SPR array 600 (as shown with RFID tag 602) or embedded in or otherwise coupled to the SPR array during manufacture (as shown with RFID 604). In various embodiments the SPR array is constructed from a standard glass slide which has a layer of gold deposited to an underside surface of the slide, and the RFID tag is adhesively applied or otherwise coupled to an upper surface 610 of the glass slide.

FIG. 7 illustrates another exemplary embodiment of a reaction plate 700 with at least one associated RFID tag. As described in connection with FIGS. 1 and 2, reaction plates such as the reaction plate 700 can be coupled to an RFID tag to facilitate the association of information with the biological contents of the reaction plate. For example, an RFID tag 702 can be applied to an exterior surface of the reaction plate 700, or an RFID tag 704 can be embedded or otherwise coupled within a portion of the reaction plate. Any reaction plate with 8, 16, 24, 48, 96 (FIG. 1), 384 (FIG. 7), 768, 1536, 3072, 6144, etc. is contemplated by the present teachings.

Figure 8:
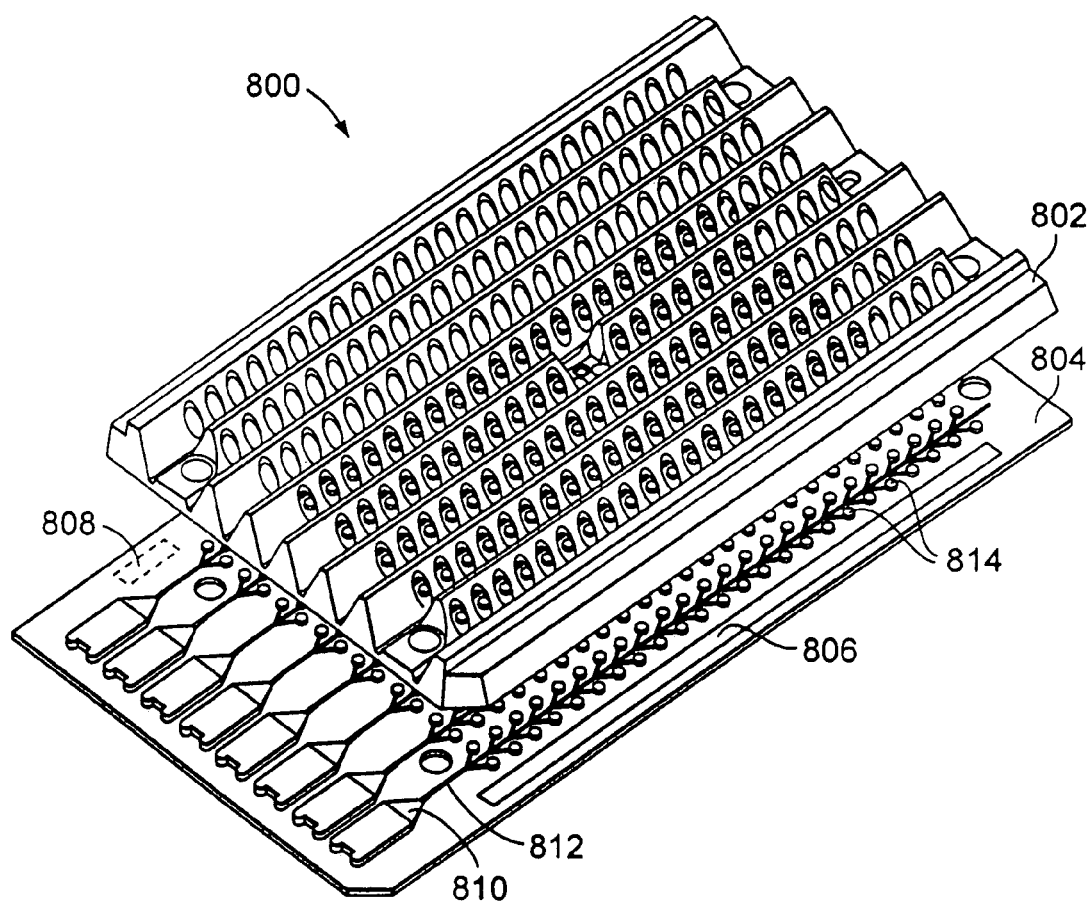
FIG. 8 illustrates an exemplary embodiment of a microfluidic card in connection with various exemplary locations for RFID tags according to various embodiments.

FIG. 8 illustrates an exemplary embodiment of a microfluidic card 800 having at least one associated RFID tag. The microfluidic card 800 provides an array containing multiple chambers 814 for testing various biological reagents on many different primer and probe sets thereby, for example, eliminating labor-intensive pipetting steps. In connection with the microfluidic card 800, biological reagents can be injected into the card via inlet ports 810 through channels 812 into the clambers 814.

According to various embodiments, information regarding the contents of the chambers and/or the contents loaded into the card can be provided. Accordingly, RFID tags consistent with the present teachings are affixed to a surface of a portion of the microfluidic card 800 for example on surface 804 as shown in connection with RFID tag 806. The RFID tag 808 is shown as being embedded into a portion of the microfluidic card 800. It is understood that the RFID tag can be affixed to, embedded in, or otherwise coupled to other portions of the card, such as the supporting lid portion 802, which has a plurality of apertures, through which the chambers 814 can be observed by an instrument to determine the results of an assay performed in connection with the microfluidic card 800. The lid portion 802 can be a part of some embodiments and not a part of other embodiments. The RFID tag 806 can include information regarding specific assays preloaded into the microfluidic card. Further, the RFID tag 806 can include information regarding samples injected into the card, which is written to the RFID tag as the samples are being injected into the card.

Figure 9:
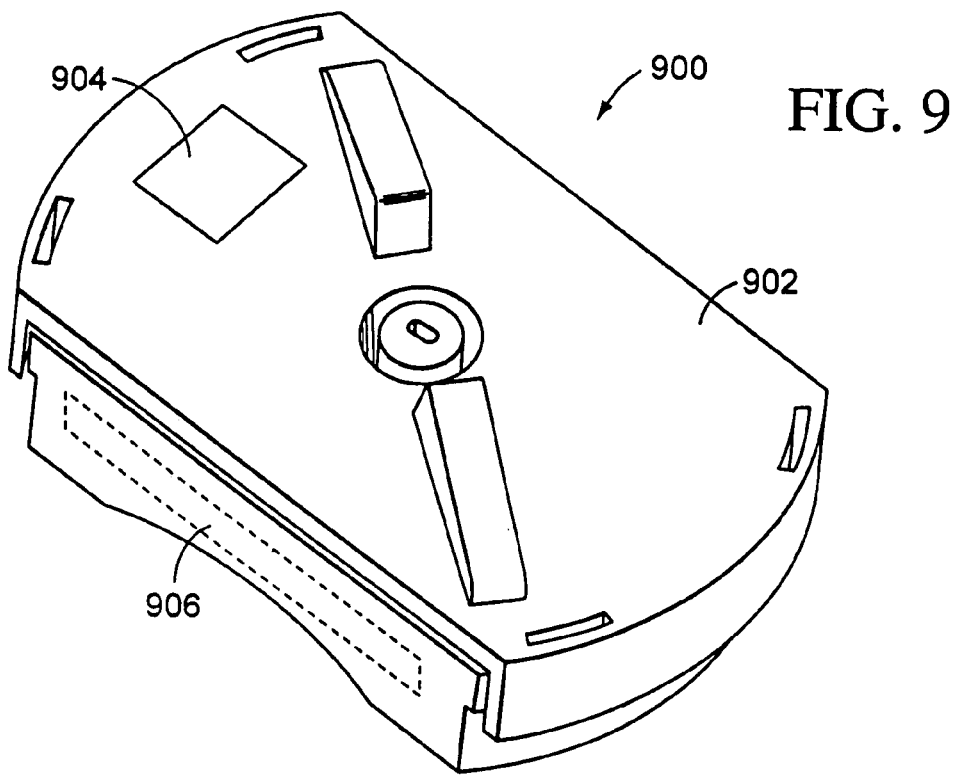
FIG. 9 illustrates an exemplary embodiment of a microarray cartridge in connection with various exemplary locations for RFID tags according to various embodiments.
Figure 10:
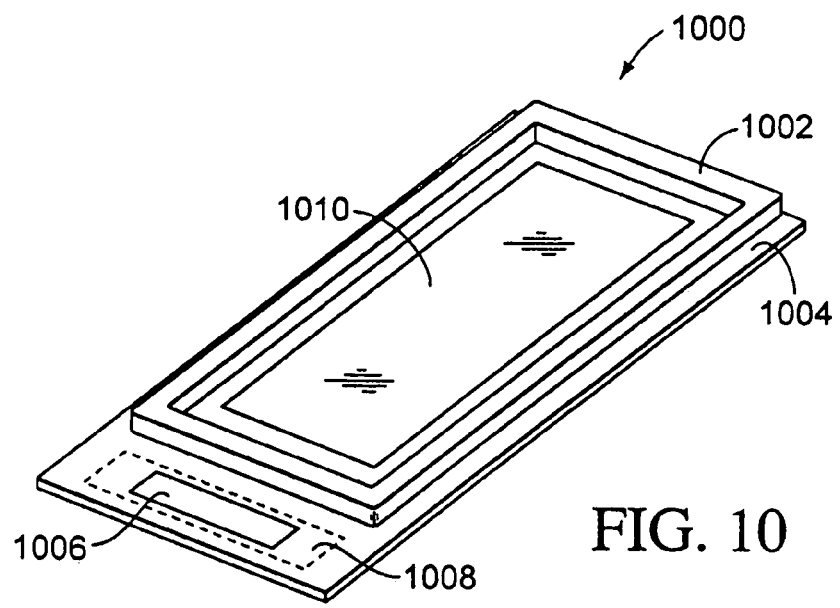
FIG. 10 illustrates an exemplary embodiment of a microarray in connection with various exemplary locations for RFID tags according to various embodiments.

FIG. 9 illustrates an exemplary embodiment of a microarray cartridge 900 with at least one associated RFID tag. The microarray cartridge 902 is provided to facilitate the protection and loading of a microarray on microarray slide 1000 as illustrated in FIG. 10. In various embodiments, the microarray cartridge 900 is substantially opaque which does not allow for the optical reading of information from the microarray slide 1000. However, consistent with the present teachings, RFID tag information can be read regarding the contents of the microarray slide 1000 even absent an optical path in the microarray cartridge 900. Additionally, information regarding the microarray contained within the microarray cartridge 900 can be stored or referenced in RFID tag 904, which can be affixed to an outer surface 902 of the microarray cartridge 900. In various embodiments, the RFID tag 906 can be embedded in or otherwise coupled to a wall portion of the microarray cartridge 900.

FIG. 10 illustrates an exemplary embodiment of the microarray slide 1000 having at least one RFID tag associated with the microarray 1010. RFID tags 1006 and 1008 are shown as alternatively being embedded in substrate 1004 or as being affixed to an outer surface portion of the substrate 1004. It is understood that RFID tags can be positioned in any convenient configuration on the microarray slide 1000, including, for example along an outer periphery of the microarray slide 1000, along an outer periphery of the gasket 1002 positioned around microarray 1010 or on an underside surface of the substrate 1004 without departing from the scope of the present teachings.

According to various embodiments, information can be stored or referenced in RFID tags associated with any of the above-described consumables that can be useful, for example, in the transportation of the biological reagents. For example, in connection with the importation and/or exportation of biological reagents, biological reagent content information, country of origin information, travel information, and/or chain of custody information can be provided consistent with the present teachings. National customs agencies typically require the provision of such country of origin information during import and/or export of various biological reagents. It is understood that the provision of such information by way of an RFID reader interface would drastically expedite the provision to customs authorities of, for example, country of origin information for various biological reagents.

Accordind to various embodiments, Material Safety Data Sheet (MSDS) information can be stored or referenced in the RFID tags and read at any time during the lifecycle of the biological reagent while it is contained in or supported by a carrier consistent with the present teachings.

According to various embodiments, the information stored in or referenced in the RFID tags associated with the biological reagents can include traverler information that is written to the RFID tag at various stages or steps along the course of a biological assay. In various embodiments, genealogy information is read and used during the course of an assay.

According to various embodiments, biological samples or reagents that are provided in the carriers described above are licensed separately from instruments designed to operate on the biological reagents. In various embodiments the instruments are coupled to a network (see e.g. FIG. 11) that allows the instruments to communicate over public and private networks with computer systems that are operated by or on behalf of the producers and/or licensors of the biological reagents. In various embodiments, reagent licenses can provide for the use of licensed biological reagents for a particular biological analysis on only licensed instruments. In various embodiments, instrument licenses can provide for the use of licensed instruments to carry out a particular biological analysis with one licensed reagents. Accordingly, an instrument can authenticate a biological reagent based on, for example, a digital signature contained in the RFID tag associated with a particular consumable, if a particular user has a valid license. In various embodiments, the RFID tags can, also be programmed to provide a one time use such that biological reagents cannot be refilled for use with the same authentication. Accordingly, an instrument can record a use of a carrier with non-licensed materials, a reuse, a use of the carrier beyond an acceptable or recommended number of uses, or usability scenarios for a carrier and/or biological reagents. An instrument can associate a carrier identification information with an approved assay, and for example, warn a user upon finding a mismatch between the approved assay and an assay to be performed. Use of the carrier in a research, laboratory, or diagnostic environment can be recorded. A user can be allowed to utilize the carrier after, for example, a warning has been generated or logged. A warranty of the carrier, instrument, and/or carrier can be voided when a warning or an error is generated.

According to various embodiments, when an RFID tag is read by an instrument that has access to a data network that includes a connection to information regarding biological reagent recall information, the instrument can perform a database lookup to determine whether the biological reagent has been subject to a recall. The recall information and an optional last recall check date and/or timestamp can be written to the RFID tag. In various embodiments, a recall database lookup is performed each time before a biological reagent is utilized in an assay or other test such as, for example a clinical diagnostic procedure.

According to various embodiments, external displays are provided to display information regarding the biological reagent contents of a consumable when the biological reagent is inside of an instrument or other container, such as a refrigerator. For example when a microarray is contained within its microarray cartridge, an RFID reader can read the identification information from the microarray and display it on a human readable interface, such as a computer terminal, LCD, or other type of display.

Figure 11:
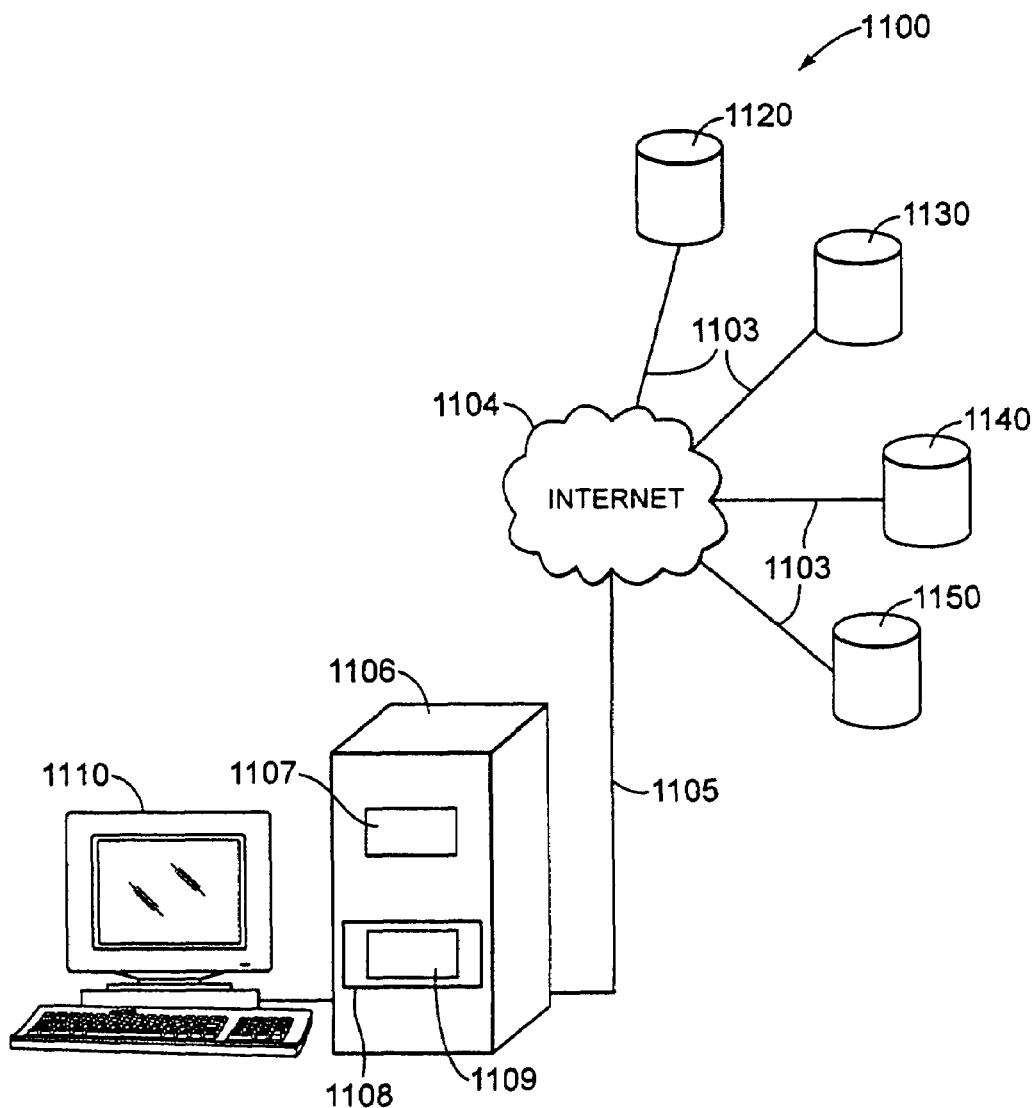
FIG. 11 illustrates an exemplary embodiment of an on-line biological instrument system according to various embodiments.

FIG. 11 illustrates an exemplary embodiment of an on-line biological instrument system 1100 consistent with the present teachings. In various embodiments, a general purpose computer 11 10 serves a function of controlling an instrument 1106 as it performs operations on biological reagents supported by carriers 1108. RFID tags 1109 that are affixed to, embedded in, or otherwise coupled to the carriers 1108 can be read by and/or written to by the RFID reader 1107. In various embodiments, the RFID reader 1107 can read identification information from the RFID tag 1109 to identify the biological reagent being supported by the carrier 1108 at particular points in time. In various embodiments, identifying descriptions, such as the name or work number associated with the biological reagent can be displayed on the monitor of the general purpose computer 1110. In various other embodiments, the identifying descriptions can be provided on a display (not shown) that is externally connected to the instrument 1106, for example, a computer built-in or integrated with an instrument, a computer on the network, or a reader not associated with an instrument. In some embodiments, the instrument can exist stand-alone on the network. In some embodiments, an instrument can comprise a built-in information display.

Via a network connection 1105, the instrument 1106, and/or the general purpose computer 1110 can be connected to a public or private network, such as internet 1104. It is understood that any networking technology can be employed without departing from the present teachings, including wired and wireless networking technologies. It is also understood that, in various embodiments, the network connection associated with the instrument 1106 can emanate from the instrument 1106 as shown and/or from the general purpose computer 1110.

By employing a network connection, the instrument 1106 and/or its associated general purpose computer 1110 can remotely access databases 1120, 1130, 1140, and 1150 via remote network connections 1103. In various embodiments, information contained in the databases 1120, 1130, 1140, and 1150 can be written to the RFID tag 1209 as set forth below in connection with FIG. 12. In various embodiments, the database 1120 can include identification information. In various embodiments, the database 1130 can include supplemental information, such as annotated information regarding a biological reagent. In various embodiments, the database 1140, can include rights information, which as set forth above can be used to authenticate or validate the biological reagent and/or determine the validity of licenses associated with the biological reagent. In various embodiments, databases 1140 can include information used to check for any product recalls associated with the biological reagent. In various embodiments, the database 1150 can contain information regarding instrument operations, log information, reference information, or other types of information listed above. In various embodiments, connections to the databases are encrypted for privacy. In various embodiments, the contents of the databases 1120, 1130, 1140, and 1150 are encrypted for confidentiality and to facilitate access control to the information contained in the databases 1120, 1130, 1140, and 1150.

According to various embodiments, the instrument 1106 includes instrument hardware, instrument firmware, instrument data acquisition and control software, and method or module data. In various embodiments, the instrument hardware includes electronic control and data processing circuitry, such as a microprocessor or microcontroller, memory, and non-volatile storage. In various embodiments, the instrument hardware also includes physical devices to manipulate biological reagents such as robotics and sample pumps. In various embodiments, the instrument firmware includes low-level, computer-readable instructions for carrying out basic operations in connection with the instrument hardware. In various embodiments, the instrument firmware includes microprocessor instructions for initializing operations on a microprocessor in the instrument hardware.

According to various embodiments, the instrument data acquisition and control software is higher-level software that interfaces with the instrument firmware to control the instrument hardware for more specific operations such as operating a charge coupled device (CCD) to acquire visual luminescence information regarding a particular biological analysis. In various embodiments the data acquisition and control software includes a software-implemented state machine providing, for example, the following states: (i) idle; (ii) running; (iii) paused; and (iv) error. In various embodiments, when the state machine is in the idle state, it can receive an instruction from the general purpose machine 1110 to perform a particular data acquisition or instrument control operation. In various embodiments, the general purpose computer 1110 opens a TCP/IP socket connection to the instrument 1106, determines whether the instrument 1106 is in the idle state and then begins transmitting instructions and/or parameters. In various embodiments, an encrypted TCP/IP connection is established, using, for example, the SSH protocol. The instructions and/or parameters can be in the form of ASCII encoded, human readable module and/or method information that defines the behavior of the biological instrument. In various embodiments, the modules and/or methods are stored or referenced in the form of ASCII text files. In various embodiments, the general purpose computer 1110 uses the FTP protocol, HTTP protocol, HTTPS protocol, or any other appropriate network protocol to transfer the ASCII text files to the instrument 1106. In various other embodiments the method and/or module information is stored or referenced in and read from the RFID tag 1109. The method and/or module information can be stored or referenced in the form of an ASCII text file in the RFID tag 1109, but it is understood that the information can be represented in other data formats without departing from the present teachings. In various embodiments, methods and module information is stored or referenced in a relational database, such as those available from the Oracle Corporation of Redwood Shores, Calif.

According to various embodiments, the module, macro, and/or method information includes parameters that can be used by the instrument data acquisition and control software to perform specific data acquisition and instrument control operations. In various embodiments, the method and/or module information contains sequences of operations to be performed by the instrument or control parameters for use in connection with the data acquisition or control software.

Figure 12:
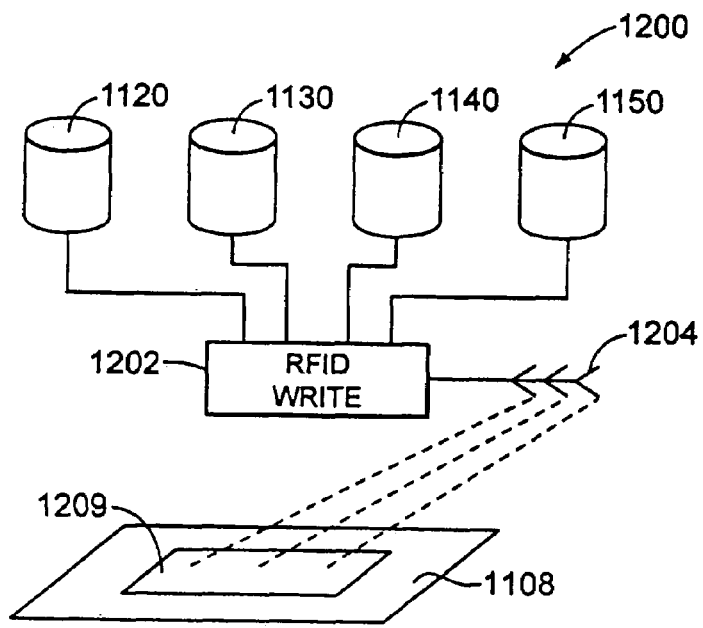
FIG. 12 illustrates an exemplary embodiment of an RFID writing apparatus according to various embodiments.

FIG. 12 illustrates an exemplary embodiment of an RFID writing apparatus 1200 consistent with the present teachings. RFID carrier 1108 is shown with an associated read/write capable RFID tag 1209. In various embodiments, an RFID reader 1202, having RFID read and write capabilities and antenna 1204, is coupled to the databases 1120, 1130, 1140, and 1150 including identification, supplemental, rights, and instrument operation information respectively. In this configuration any combination of identification, supplemental, rights, and/or instrument operation information can be written to the RFID tag 1209 consistent with the present teachings.

Figure 13:
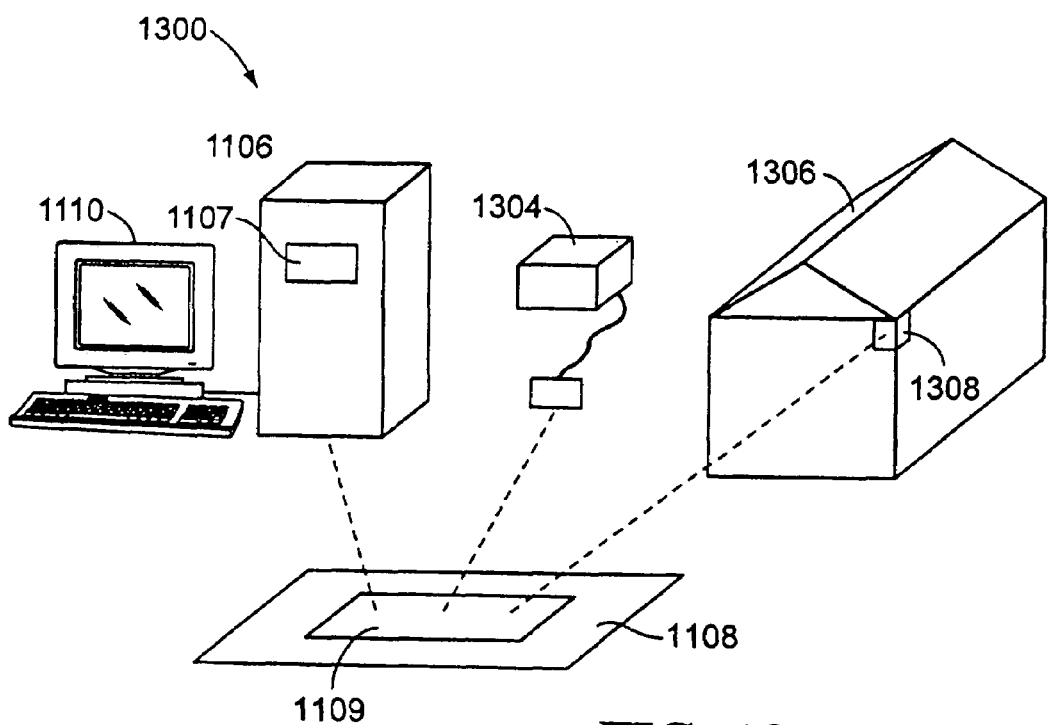
FIG. 13 illustrates an exemplary embodiment of RFID tag tracking systems according to various embodiments.

FIG. 13 illustrates an exemplary embodiment of RFID tag tracking systems 1300 consistent with the present teachings. A warehouse 1306 or manufacturing facility includes one or more RFID readers 1308, which can be used to read RFID tags on carriers such as carrier 1108 as the carriers move throughout the warehouse 1306 or manufacturing facility. The RFID readers 1308 can be used for inventory control and to provide real-time product location information. In various embodiments an instrument 1106 can perform operations on a biological reagent being supported by the carrier 1108, while the RFID reader 1308 provides general location information regarding a location of the carrier 1108. Moreover, the external RFID reader 1304 can read from and/or write information into the RFID tag 1109. In various embodiments, external, hand-held RFID readers such as the RFID reader 1304 can be used to write to or read information from the RFID tags 1109. According to various embodiments, obtaining the real-time physical location coordinates of a carrier can be achieved by receiving GPS coordinates from a GPS receiver physically coupled to the carrier.

The section headings used herein are for organizational purposes only and are not to be construed as limiting the subject matter described in any way.

All literature and similar materials cited in this application, including but not limited to, patents, patent applications, articles, books, treatises, and internet web pages, regardless of the format of such literature and similar materials, are expressly incorporated by reference in their entirety for any purpose.

Other embodiments will be apparent to those skilled in the art from consideration of the present specification and practice of various embodiments disclosed herein. It is intended that the present specification and examples be considered as exemplary only.

What is claimed is:

1. A method for associating information with a carrier, the method comprising:
    providing a carrier adapted to retain at least one biological reagent, the carrier being coupled to an RFID tag, wherein the RFID tag is operable to be read by an RFID reader;
    receiving, from the RFID tag, an information pointer; and
    resolving the information pointer into information associated with the carrier; and
    authorizing under terms of a license, use of the carrier.

2. The method of claim 1, further comprising storing in the RFID tag permission control information pertaining to the carrier.

3. The method of claim 1, wherein the carrier retains at least one biological reagent, and the method further comprises storing information pertaining to the at least one biological reagent by writing a chronicle using the information pointer, while or after the at least one biological reagent is utilized in a biological assay.

4. The method of claim 1, further comprising storing chain of custody information regarding the carrier.

5. The method of claim 1, wherein the carrier retains at least one biological reagent, and the method further comprises genealogical information pertaining to the at least one biological reagent.

6. A method for associating information with a carrier, the method comprising:
    providing a carrier adapted to retain at least one biological reagent, the carrier being coupled to an RFID tag, wherein the RFID tag is operable to be read by an RFID reader;
    receiving, from the RFID tag, an information pointer;

resolving the information pointer into information associated with the carrier;
authorizing under terms of a license, use of the carrier;
receiving license identifier information from the information;
authenticating the license identifier information; and
based on the authenticated license identifier information, permitting the performance of at least one licensed activity in connection with the carrier.

7. The method of claim 1, further comprising validating integrity of the carrier for use in connection with a specific biological assay.

8. The method of claim 6, further comprising storing in the RFID tag permission control information pertaining to the carrier.

9. The method of claim 6, wherein the carrier retains at least one biological reagent and the method further comprises storing information pertaining to the at least one biological reagent by writing a chronicle using the information pointer, while or after the at least one biological reagent is utilized in a biological assay.

10. The method of claim 6, further comprising storing chain of custody information regarding the carrier.

11. The method of claim 6, wherein the carrier retains at least one biological reagent, and the method further comprises genealogical information pertaining to the at least one biological reagent.

12. The method of claim 6, further comprising validating integrity of the carrier for use in connection with a specific biological assay.

* * * * *